(12) United States Patent
De Ridder (10) Patent No.: US 10,035,021 B2
(45) Date of Patent: *Jul. 31, 2018

(54) USE OF A NEW STIMULATION DESIGN TO TREAT NEUROLOGICAL DISORDER

(71) Applicant: Dirk De Ridder, Dunedin (NZ)

(72) Inventor: Dirk De Ridder, Dunedin (NZ)

(*) Notice: Subject to any disclaimer, the term of this patent is extended or adjusted under 35 U.S.C. 154(b) by 0 days.

This patent is subject to a terminal disclaimer.

(21) Appl. No.: 15/299,827

(22) Filed: Oct. 21, 2016

(65) Prior Publication Data

US 2017/0189691 A1 Jul. 6, 2017

Related U.S. Application Data

(63) Continuation of application No. 14/176,672, filed on Feb. 10, 2014, now Pat. No. 9,498,634, which is a continuation of application No. 13/221,548, filed on Aug. 30, 2011, now Pat. No. 8,682,441.

(60) Provisional application No. 61/378,249, filed on Aug. 30, 2010.

(51) Int. Cl.
*A61N 1/36* (2006.01)
*A61N 1/05* (2006.01)
*A61B 5/0476* (2006.01)

(52) U.S. Cl.
CPC ........ *A61N 1/36196* (2013.01); *A61B 5/0476* (2013.01); *A61N 1/0529* (2013.01); *A61N 1/0551* (2013.01); *A61N 1/361* (2013.01); *A61N 1/36075* (2013.01); *A61N 1/36082* (2013.01)

(58) Field of Classification Search
CPC ............... A61N 1/36; A61N 1/34; A61N 1/32
USPC ...................................... 607/46, 73
See application file for complete search history.

(56) References Cited

U.S. PATENT DOCUMENTS

| | | | | |
|---|---|---|---|---|
| 4,338,945 A * | 7/1982 | Kosugi | ............. | A61N 1/36021 607/46 |
| 8,682,441 B2 * | 3/2014 | De Ridder | ......... | A61N 1/36075 607/46 |
| 9,498,634 B2 * | 11/2016 | De Ridder | ......... | A61N 1/36075 |

* cited by examiner

Primary Examiner — Carl H Layno
Assistant Examiner — Jon Eric C Morales (57) ABSTRACT

The method and system described herein relate to stimulating nerve tissue using a pulse generator. A stimulus is created that comprises a signal that is produced from a frequency spectrum having a power spectral density per unit of bandwidth proportional to $1/f^\beta$, wherein $\beta$ is excludes 0. The stimulus is provided from the pulse generator to at least one stimulation lead; and applied to nerve tissue via one or several electrodes.

12 Claims, 8 Drawing Sheets

USE OF A NEW STIMULATION DESIGN TO TREAT NEUROLOGICAL DISORDER

CROSS-REFERENCE TO RELATED APPLICATIONS

This application is a continuation of U.S. patent application Ser. No. 14/176,672, filed Feb. 10, 2014 (now U.S. Pat. No. 9,498,634) which is a continuation of U.S. patent application Ser. No. 13/221,548, filed Aug. 30, 2011 (now U.S. Pat. No. 8,682,441), which claims the benefit of U.S. Provisional Application No. 61/378,249, filed Aug. 30, 2010, which are incorporated herein by reference.

TECHNICAL FIELD

The present invention relates to a method which can be utilized to treat neurological conditions and/or disorders. More particularly, and not by way of limitation, the present invention is directed to a method for using $1/f^\beta$ noise to treat neurological conditions and/or disorders.

BACKGROUND OF THE INVENTION

Different firing modes or frequencies occur in the brain and/or other neuronal tissue, for example tonic firing and burst firing (irregular or regular burst firing). Such firing modes can be utilized for normal processing of information, however, alteration of the firing modes, may also lead to pathology.

For example, certain neurological conditions are associated with hyperactivity of the brain and can be traced to a rhythmic burst firing or high frequency tonic firing or hypersynchronous firing (e.g., tinnitus pain, and epilepsy). Other conditions can be associated with an arrhythmic burst firing or a dysynchronous firing, for example, movement disorders, hallucinations, persistent vegetative state (PVS), multiple chemical sensitivity (MCS), or hypofunctioning for example, hypoesthesia, depression, hearing loss, visual loss, dysthymia, chronic fatigue etc.

During the past decade, neuromodulation systems have been used to modulate various areas of the brain, spinal cord, or peripheral nerves (See, for example, U.S. Pat. Nos. 6,671,555; 6,690,974). These types of systems utilize tonic forms of electrical stimulation. Recently burst transcranial magnetic stimulation (TMS) at theta frequencies has been developed (Huang et al, 2005). Theta burst TMS has been shown to produce an effect on motor and visual cortex by suppressing excitatory circuits after a short application period of only 20490 s (Huang et al., 2005; Di Lazzaro et al., 2005; Franca et al., 2006).

Typically, the signals generated by the neuromodulation devices are not physiological similar to the endogenous electrical signals generated by the brain and the exogenous electrical signals generated by the neuromodulation devices typically result in epileptic events as well as the brain habituates to these electrical signals in time. The inventor is the first to describe a neuromodulation design using parameters in which a $1/f^\beta$ noise is used to achieve stimulation of the tissue close to physiological levels to treat a neurological condition.

BRIEF SUMMARY OF THE INVENTION

The method and system described herein relate to stimulating nerve tissue to treat a neurological disease and/or condition. Using a pulse generator, a stimulus is created that comprises a signal that is produced from a frequency spectrum having a power spectral density per unit of bandwidth proportional to $1/f^\beta$, wherein $\beta$ excludes 0. $\beta$ can be, for example, any real, natural, integer, rational, irrational complex or fluctuating number. For example, $\beta=1$ or $\beta=2$. The stimulus is provided from the pulse generator to at least one stimulation lead; and applied to nerve tissue of the patient via one or several electrodes of the at least one stimulation lead.

Yet further, the stimulus can be combined with at least one pulse stimulus repeated in a tonic manner or a burst stimulus that comprises a plurality of groups of spike pulses.

Still further, the stimulus can be modulated at any specific frequency, either by selective power increase, envelope modulation or adding more tonic or burst stimuli of this frequency.

A first stimulation parameter that defines a frequency having a lower bound of a frequency spectrum and a second stimulation that defines a frequency having an upper bound of a frequency spectrum can be stored in a controller or pulse generator and such controller can be used to generate a stimulus that comprises a frequency spectrum between the first and second stimulation parameters such that the frequency and power of the frequency spectrum are inversely proportional.

BRIEF DESCRIPTION OF THE SEVERAL VIEWS OF THE DRAWING

In the following section, the invention will be described with reference to exemplary embodiments illustrated in the figures, in which:

FIGS. 3A and 3B illustrate pink noise or 1/f noise. FIGS. 4A and 4B illustrate red, brown or Brownian noise or $1/f^2$ noise.

FIGS. 5A-5B illustrate exemplary combinations of $1/f^\beta$ noise.

DETAILED DESCRIPTION OF THE INVENTION

The following section more generally describes an example of a procedure for treatment using a $1/f^\beta$ noise such as pink noise, red or brown noise or black noise to optimize the following parameters; a set and/or range of stimulation protocols that can most completely eliminate neurological disease/disorder, a set and/or range of stimulation protocols that requires the lowest voltage, and a protocol that maintains treatment efficacy over long periods of time, for example, the protocol can prevent habituation or adaptation and a protocol that is anti-epileptic. Still further, the generated $1/f^\beta$ noise signal can be filtered, combined, or otherwise processed, for example, whereby the generated $1/f^\beta$ noise is utilized as a background signal noise over another signal with a spectral peak at a selected frequency. For example, an alpha peak, beta peak, delta peak and/or theta peak can be added to the $1/f^\beta$ noise. The peaks can be generated using typical known frequencies or the peaks can be individualized for each patient. Yet further, the $1/f^\beta$ noise can be combined with standard tonic and/or burst stimulation to further enhance the optimization or prevent habituation. Combinations of tonic and/or burst stimulation are known in the art, for example, U.S. Pat. No. 7,734,340, issued Jun. 8, 2010 and U.S. application Ser. No. 12/109,098, filed Apr. 24, 2008, which are incorporated by reference in their entirety.

The predetermined site for stimulation can include, for example, peripheral neuronal tissue and/or central neuronal tissue. Peripheral neuronal tissue can include a nerve root or root ganglion or any peripheral neuronal tissue associated with a given dermatome or any neuronal tissue that lies outside the brain, brainstem or spinal cord.

I. $1/f^\beta$ Noise

A noise signal can be described as a signal that is generated according to a random process. In practice, various algorithms (e.g., in software executed on a processor) are employed to simulate a given random process to generate a "pseudo-random" signal where the generated pseudo-random signal possesses similar characteristics with signals corresponding to a corresponding random process. The characteristics of a particular noise signal depend upon the underlying process generating the noise signal. For example, the power spectral density or power distribution in the frequency domain may be employed to characterize the random process and, hence, also characterize a corresponding time-domain noise signal. The classification of the power spectral density of a noise signal may be described in reference to color or color terminology with different types of power spectral densities named after different colors.

According to these conventions, the power spectral density is defined as being inversely proportional to $f^\beta$, where f represents frequency and β is a value selected to characterize the noise signal. The value β can be for example, any real, natural, integer, rational, irrational or complex number. For example, the spectral density for white noise is flat (β=0), for pink noise or flicker noise β=1 and for Brownian or red noise β=2 and black noise is β>2. Suitable non-integer β values about 1 include 0.5, 0.6, 0.7, 0.8, 0.9, 1.0, 1.1, 1.2, 1.3, 1.5, or any values there between for some embodiments. Likewise, suitable non-integer β values about 2 can include 1.6, 1.7, 1.8, 1.9, 2.0, 2.1, 2.2, 2.3, 2.4, 2.5 or any value there between for some embodiments.

Abnormal electrical and/or neural activity is associated with different diseases and disorders hi the central and peripheral nervous systems. In addition to a drug regimen or surgical intervention, potential treatments for such diseases and disorders include the implantation of a medical device (for example, an implantable pulse generator (IPG)) in a patient for electrical stimulation of the patient's body tissue. In particular, an implantable medical device may electrically stimulate a target neuronal tissue location by the selective application of controlled electrical input signals to one or more electrodes coupled to or placed in proximity to the patient's neuronal tissue. Such electrical input signals may be applied to the patient's neuronal tissue in order to treat a neurological disease, condition, or disorder.

The response of nonlinear systems to a weak input signal may be optimized by combining the input signal with a non-negligible level of noise or as known in the art as stochastic resonance. For a system to exhibit stochastic resonance there needs to be a threshold that must be exceeded in order to activate the system. When the input signal is not strong enough to exceed the threshold, small amounts of noise added either to the system or the signal may occasionally suffice to trigger activation. Typically this type of phenomenon is associated with white noise.

Over time, a repetitive electrical stimulation signal, such as typical electrical stimulation performed today, that is dissimilar to the brain's own naturally-occurring signals may become less effective as the brain "filters outs" or "ignores" the signal. Hence, a problem with standard electrical stimulation parameters used today is habituation because the electrical stimulation parameters result in a repetitive electrical signal and thus, the brain habituates to the signal or adapts. It is believed that naturally-occurring signals within the human brain closely resemble $1/f^\beta$ noise. Because of this, the efficacy of electrical stimulation signals applied to neuronal tissue is improved by making those signals comport as closely as possible to the brain's own signals. Such a signal may be less likely to lose effectiveness over time. One way to comport an electrical stimulation signal to resemble the brain's own signals is to utilize a stimulation paradigm that resembles that of the brain's normal signals, for example convert the pink noise spectrum into electrical stimulation signals that can be applied to the desired neuronal tissue at a desired pattern, frequency, amplitude such that it maintains parameters associated with $1/f^\beta$ noise spectrum. To further modulate the $1/f^\beta$ noise stimulation paradigm, add specific peak frequencies to the $1/f^\beta$ noise stimulation paradigm that are known or associated with given brain areas, for example, add an alpha frequency peak to stimulate primary and secondary cortical areas; add a beta frequency peak to stimulate association cortical areas, such as frontal cortex; add a theta frequency peak to stimulate the cingulate, hippocampus, amygdala; add a delta frequency peak to stimulate the brainstem, ventral tegmental area (VTA), nucleus accumbens/ventral medial prefrontal cortex (VMPFC). Yet further, black noise can be used to stimulate the brainstem and/or the reward system. These additional peak frequencies that are added to the $1/f^\beta$ noise stimulation paradigm can be obtained from the individual by EEG or MEG measurements or any other measurement to obtain the individual peak frequency or the frequencies can be obtained from a database, for example a database containing a list of given frequencies and spectral structures for a brain structure or brain area. The frequency for each brain area, for example, each Brodmann area can be easily calculated by defining a Brodmann area in source space and performing a spectral analysis for that area using any software (i.e., sLORETA) to perform source analysis.

Still further, the $1/f^\beta$ noise stimulation paradigm can be modified by using multiple poles or electrodes, for example, the stimulation paradigm is either sequentially cycled or randomly cycles through the poles or electrodes upon the stimulation lead.

The $1/f^\beta$ noise can also be selected to specifically activate or inactivate a brain area or brain network, i.e., it can be chosen so as to not be normalizing, but to be non-physiological as to compensate for overactivity or hypoactivity, followed at a later stage with normal physiological $1/f^\beta$ noise stimulation parameters. For example during sleep, changing the $1/f^\beta$ noise during sleep can improve memory storage or prevent storage of memories, i.e., to prevent or treat post-traumatic stress disorder (PTSD).

II. Patient Selection

Subjects to be treated according to some representative embodiments can be selected, identified and/or diagnosed based upon the accumulation of physical, chemical, and historical behavioral data on each patient. One of skill in the art is able to perform the appropriate examinations to accumulate such data. One type of examination can include neurological examinations, which can include mental status evaluations, which can further include a psychiatric assessment. Other types of assessments for movement disorders may include such assessments for example using the Unified Parkinson's Disease Rating Scale (UPDRS), further, other types of examinations can include, but are not limited to, motor examination, cranial nerve examination, cognitive assessment and neuropsychological tests (i.e. Minnesota Multiphasic Personality Inventory, Beck Depression Inventory, or Hamilton Rating Scale for Depression). Other types of assessment for tinnitus, for example, can include but are not limited to Visual Analogue Scales (VAS) and Tinnitus Handicap Inventory (THI). In addition to neurological testing, routine hematological and/or biochemistry testing may also be performed.

In addition to the above examinations, imaging techniques can be used to determine normal and abnormal brain function that can result in disorders. Thus, once the patient is identified from the above clinical examinations, imaging techniques can be further utilized to provide the region of interest in which the electrodes are to be implanted. Functional brain imaging allows for localization of specific normal and abnormal functioning of the nervous system. This includes electrical methods such as electroencephalography (EEG), magnetoencephalography (MEG), single photon emission computed tomography (SPECT), as well as metabolic and blood flow studies such as functional magnetic resonance imaging (fMRI), and positron emission tomography (PET) which can be utilized to localize brain function and dysfunction.

III. Implantation of Stimulation Leads

One or more stimulation leads 100, as shown in FIGS. 1A-1J are implanted such that one or more stimulation electrodes 102 of each stimulation lead 200 are positioned or disposed near, adjacent to, directly on or onto, proximate to, directly in or into or within the target tissue or predetermined site. The leads shown in FIG. 1 are exemplary of many commercially available leads, such as deep brain leads, percutaneous leads paddle leads, etc. Examples of commercially available stimulation leads includes a percutaneous OCTRODE® lead or laminotomy or paddle leads or paddle structures such as PENTA® lead or LAMITRODE 44® lead all manufactured by Advanced Neuromodulation Systems. Inc. For the purposes described herein and as those skilled in the art will recognize, when an embedded stimulation system, such as the Bion®, is used, it is positioned similar to positioning the lead 100.

Techniques for implanting stimulation electrodes are well known by those of skill in the art and may be positioned in various body tissues and in contact with various tissue layers; for example, deep brain, cortical, subdural, subarachnoid, epidural, cutaneous, transcutaneous and subcutaneous implantation is employed in some embodiments.

A. Brain

Central neuronal tissue includes brain tissue, spinal tissue or brainstem tissue. Brain tissue can include the frontal lobe, the occipital lobe, the parietal lobe, the temporal lobe, the cerebellum, or the brain stem. More specifically, brain tissue can include subcortical targets, for example, thalamus/subthalamus (i.e. thalamic nuclei, medial and lateral geniculate body, intralaminar nuclei, nucleus reticularis, pulvinar, subthalamic nuclei (STN), etc) basal ganglia (i.e., putamen, caudate nucleus, globus pallidus), hippocampus, amygdala hypothalamus, epithalamus, mammilary bodies, ventral tegmental area (VIA), substantia nigra, corpus callosum, fornix, internal capsula, anterior and posterior commissural, cerebral peduncles etc. Brain tissue also includes cerebellum, cerebellar peduncles, and cerebellar nuclei such as fastigial nucleus, globose nucleus, dentate nucleus, emboliform nucleus. Still further, in addition to the above mentioned subcortical targets, brain tissue also includes cortical targets, for example, auditory cortex, prefrontal cortex, the dorsolateral prefrontal cortex, the ventromedial prefrontal cortex, the cingulate cortex, subcallosal area, anterior cingulate cortex, the subgenual anterior cingulate cortex, the motor cortex and the somatosensory cortex. The somatosensory cortex comprises the primary, the secondary somatosensory cortex, and the somatosensory association complex. Still further, the somatosensory cortex also includes Brodmann areas 1, 2, 3, 5, and 7. Yet further, brain tissue can include various Brodmann areas for example, but not limited to Brodmann area 9, Brodmann area 10, Brodmann area 24, Brodmann area 25, Brodmann area 32, Brodmann area 39, Brodmann area 41, Brodmann area 42, and Brodmann area 46.

While not being bound by the description of a particular procedure, patients who are to have an electrical stimulation lead or electrode implanted into the brain for deep brain stimulation generally first have a stereotactic head frame, such as the Leksell, CRW, or Compass, mounted to the patient's skull by fixed screws. Subsequent to the mounting of the frame, the patient typically undergoes a series of magnetic resonance imaging sessions, during which a series of two dimensional slice images of the patients brain are built up into a quasi-three dimensional map in virtual space. This map is then correlated to the three dimensional stereotactic frame of reference in the real surgical field. In order to align these two coordinate frames, both the instruments and the patent must be situated in correspondence to the virtual map. The current way to do this is to rigidly mount the head frame to the surgical table. Subsequently, a series of reference points are established to relative aspects of the frame and patient's skull, so that either a person or a computer software system can adjust and calculate the correlation between the real world of the patient's head and the virtual space model of the patient MRI scans. The surgeon is able to target any region within the stereotactic space of the brain with precision (e.g., within 1 mm). Initial anatomical target localization is achieved either directly using the MRI images or functional imaging (PET or SPECT scan, fMRI, MSI), or indirectly using interactive anatomical atlas programs that map the atlas image onto the stereotactic image of the brain. As is described in greater detail elsewhere in this application, the anatomical targets or predetermined site may be stimulated directly or affected through stimulation in another region of the brain.

In addition to deep brain stimulation cortical stimulation can also be used to stimulate various brain tissues. Any of the stimulation leads illustrated in FIGS. 1A-1J can be used for cortical stimulation, as well as any other cortical electrode or electrode array. For implanting conventional cortical electrodes, it typically requires a craniotomy under general anesthesia to remove a relatively large (e.g., thumbnail-sized or larger) window in the skull. A pilot hole (e.g., 4 mm or smaller) can be formed through at least part of the thickness of the patient's skull adjacent a selected or predetermined site. In certain embodiments, the pilot hole can be used as a monitoring site.

The location of the pilot hole (and, ultimately the electrode received therein) can be selected in a variety of fashions, for example the physician may use anatomical landmarks, e.g., cranial landmarks such as the bregma or the sagittal suture, to guide placement and orientation of the pilot hole or the physician may use a surgical navigation system. Navigation systems may employ real-time imaging and/or proximity detection to guide a physician in placing the pilot hole and in placing the electrode in the pilot hole, in some systems, fiducials are positioned on the patient's scalp or skull prior to imaging and those fiducials are used as reference points in subsequent implantation. In other systems, real-time MRI or the like may be employed instead of or in conjunction with such fiducials. A number of suitable navigation systems are commercially available, such as the STEALTHSTATION TREON TGS sold by Medtronic Surgical Navigation Technologies of Louisville, Colo., U.S.

Once the pilot hole is formed, the threaded stimulation lead may be advanced along the pilot hole until the contact surface electrically contacts a desired portion of the patient's brain. If the stimulation lead is intended to be positioned epidurally, this may comprise relatively atraumatically contacting the dura mater; if the electrode is to contact a site on the cerebral cortex, the electrode will be advanced to extend through the dura mater. Thus, the lead may be placed epidurally or subdurally for cortical stimulation.

B. Spinal Cord and/or Peripheral Nerves

Peripheral nerves can include, but are not limited to olfactory nerve, optic nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, occipital nerve (e.g., suboccipital nerve, the greater occipital nerve, the lesser occipital nerve), the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, illoinguinal nerves, gentofemoral nerves, and iliohypogastric nerves. Furthermore, peripheral neuronal tissue can include but is not limited to peripheral nervous tissue associated with a dermatome.

Spinal tissue can include the ascending and descending tracts of the spinal cord, more specifically, the ascending tracts of that comprise intralaminar neurons or the dorsal column. For example, the spinal tissue can include neuronal tissue associated with any of the cervical vertebral segments (C1, C2, C3, C4, C5, C6, C7 and C8) and/or any tissue associated with any of the thoracic vertebral segments (T1, T2, T3, T4, T5, T6, T7, T8, T9, T10, T11, T12) and/or any tissue associated with any of the lumbar vertebral segments (L1, L2, L3, L4, L5, L6) and/or any tissue associated with the sacral vertebral segments (S1, S2, S3, S4, S5). More specifically, the spinal tissue is the dorsal column of the spinal cord. The brainstem tissue can include the medulla oblongata, pons or mesencephalon, more particular the posterior pans or posterior mesencephalon, Lushka's foramen, and ventrolateral part of the medulla oblongata.

In other embodiments, the stimulation leads are positioned in communication with the neuronal tissue of the spinal cord, more specifically, the dorsal column of the spinal cord. For example, stimulation electrodes are commonly positioned external to the dura layer surrounding the spinal cord. Stimulation on the surface of the cord is also contemplated, for example, stimulation may be applied to the spinal cord tissue as well as to the nerve root entry zone. Stimulation electrodes may be positioned in various body tissues and hi contact with various tissue layers; for example, subdural, subarachnoid, epidural, and cutaneous, and/or subcutaneous implantation is employed in some embodiments.

Spinal cord stimulation can be accomplished utilizing either percutaneous leads and/or laminotomy type leads that comprise a paddle. Percutaneous leads commonly have two or more equally-spaced electrodes which are placed above the dura layer through the use of a Touhy-like needle. For insertion, the Touhy-like needle is passed through the skin between desired vertebrae to open above the dura layer.

In contrast to the percutaneous leads, laminotomy leads have a paddle configuration and typically possess a plurality of electrodes (for example, two, four, eight, sixteen or twenty) arranged in one or more columns. Implanted laminotomy leads are commonly transversely centered over the physiological midline of a patient. In such position, multiple columns of electrodes are well suited to address both unilateral and bilateral pain, where electrical energy may be administered using either column independently (on either side of the midline) or administered using both columns to create an electric field which traverses the midline. A multi-column laminotomy lead enables reliable positioning of a plurality of electrodes, and in particular, a plurality of electrode columns that do not readily deviate from an initial implantation position.

Laminotomy leads require a surgical procedure for implantation. The surgical procedure, or partial laminectomy, requires the resection and removal of certain vertebral tissue to allow both access to the dura and proper positioning of a laminotomy lead. The laminotomy lead offers a more stable platform, which is further capable of being sutured in place that tends to migrate less in the operating environment of the human body. Depending on the position of insertion however, access to the dura may only require a partial removal of the ligamentum flavum at the insertion site. In some embodiments, two or more laminotomy leads may be positioned within the epidural space, and the leads may assume any relative position to one another.

In certain embodiments, the stimulation leads may be placed subcutaneously on the patient's head. For example, one or more stimulation leads can be implanted subcutaneously such that one or more stimulation electrodes are positioned in communication with a dermatome area, for example (C1, C2, C3, C4, C5, C6, C7, and C8), cervical nerve roots (e.g., C1, C2, C3, C4, C5, C6, C7 and C8) cranial nerves (e g, olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and hypoglossal nerve) and/or occipital area For example, one or more stimulation electrodes are positioned in the C2 dermatome area/C3 dermatome area, subcutaneously, but superior to the galea. Within certain areas of the C2 dermatome area or occipital or occiput area, there is little or no muscle this area primarily consists of fat, fascia, perostium, and neurovascular structures (e.g., galea). More specifically, the electrode can be implanted in a subcutaneous fashion such that the electrode is positioned below the skin, above the bone on the back of the head or superior to the periosteum. On the back of the head, the probe is positioned in the C2 dermatome area or positioned at the back of the patient's head at about the level of the ear.

C. Brainstem Stimulation

Implantation of a stimulation lead in communication with the predetermined brainstem area can be accomplished via a variety of surgical techniques that are well known to those of skill in the art. For example, an electrical stimulation lead can be implanted on, in, or near the brainstem by accessing the brain tissue through a percutaneous route, an open craniotomy, or a burr hole. Where a burr hole is the means of accessing the brainstem, for example, stereotactic equipment suitable to aid in placement of an electrical stimulation lead on, in, or near the brainstem may be positioned around the head. Another alternative technique can include, a modified midline or retrosigmold posterior fossa technique.

In certain embodiments, electrical stimulation lead is located at least partially within or below the dura mater adjacent the brainstem. Alternatively, a stimulation lead can be placed in communication with the predetermined brainstem area by threading the stimulation lead up the spinal cord column, as described above, which is incorporated herein.

Still further, a predetermined brainstem area can be indirectly stimulated by implanting a stimulation lead in communication with a cranial nerve (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and the hypoglossal nerve) as well as high cervical nerves (cervical nerves have anastomoses with lower cranial nerves) such that stimulation of a cranial nerve indirectly stimulates the predetermined brainstem tissue. Such techniques are further described in U.S. Pat. Nos. 6,721,603; 6,622,047; and 5,335,657 each of which are incorporated herein by reference.

IV. Generation of Stimulation Parameters and Modifications Thereof

Conventional neuromodulation devices can be modified to apply a $1/f^\beta$ noise stimulation, or $1/f^\beta$ noise stimulation in combination with individual peak frequencies (e.g., alpha, beta, theta and delta) or combination of $1/f^\beta$ noise stimulation combined with burst or tonic stimulation to nerve tissue of a patient by modifying the software instructions and/or stimulation parameters stored in the devices. Specifically, conventional neuromodulation devices typically include a microprocessor and a pulse generation module. The pulse generation module generates the electrical pulses according to a defined pulse width and pulse amplitude and applies the electrical pulses to defined electrodes through switching circuitry and the wires of a stimulation lead. The microprocessor controls the operations of the pulse generation module according to software instructions stored in the device and accompanying stimulation parameters. Examples of commercially available neuromodulation devices that can be modified according to some embodiments include the EON® or EON Mini®, manufactured by St. Jude Medical. Other neuromodulation devices that may be modified can include, LIBRA® or BRIO® manufactured by St. Jude Medical.

Figure 3A:
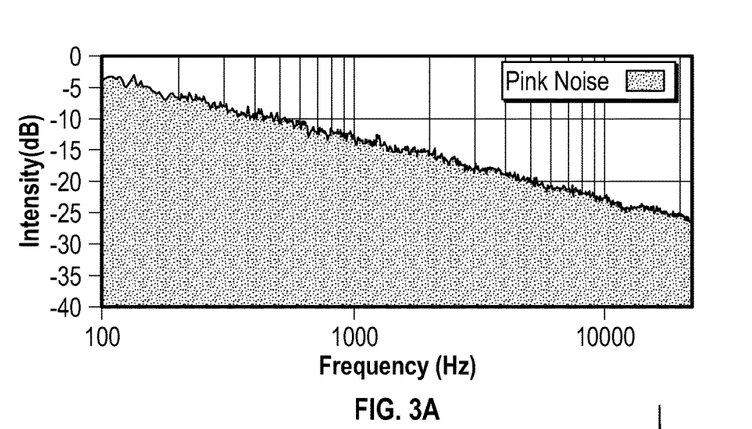
FIG. 3A shows an exemplary pink noise spectrum.
Figure 4A:
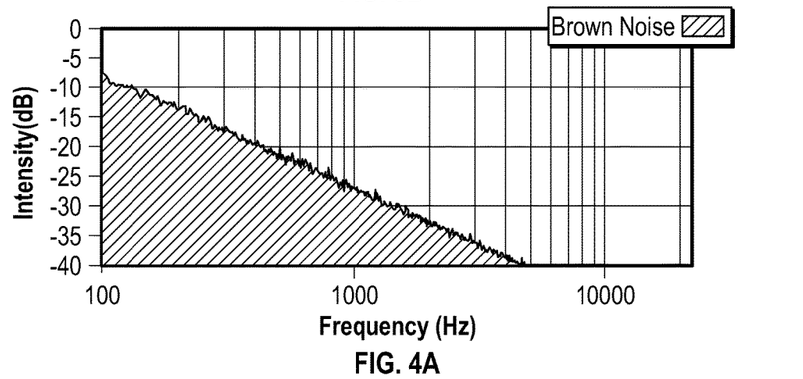
FIG. 4A shows an exemplary red or Brown (ian) noise spectrum.

These neuromodulation devices can be adapted by modifying the software instructions provided within the neuromodulation devices used to control the operations of the devices. In some embodiments, software is provided within the neuromodulation device to retrieve or generate a stream of digital values that define a waveform according to the desired power spectral density. This stream of values is then employed to control the amplitude of successive stimulation pulses generated by the neurostimulation device. The software may include a pseudo-random number generator according to known algorithms to generate the stream of digital values. Alternatively, one or more streams of digital values having the desired power spectral density may be generated offline and stored in memory of the neuromodulation device (in a compressed or other suitable format). The software of the neuromodulation device may retrieve the values from memory for control of the amplitude of the output pulses of the neuromodulation device. Alternatively, an external conventional neuromodulation devices can be used (for example, the DS8000™ digital stimulator available from World Precision Instruments) to generate the desired electrical stimulation. For example, a custom waveform may be generated offline on a personal computer and imported into the digital stimulator for pulse generation. Signal parameters may be inputted, such as $1/f^\beta$ noise spectrum, for example FIG. 3A or FIG. 4A, into suitable waveform generating software to generate the stream of digital values. Alternatively, depending upon the capabilities of the external digital stimulator, the stream of digital values may be calculated on board the processor of the external digital stimulator.

Figure 1A:
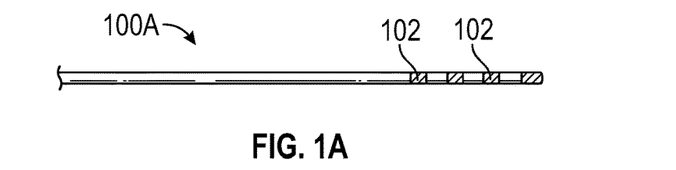
FIGS. 1A-1J illustrate example electrical stimulation leads that may be used to electrically stimulate neuronal tissue.
Figure 1B:
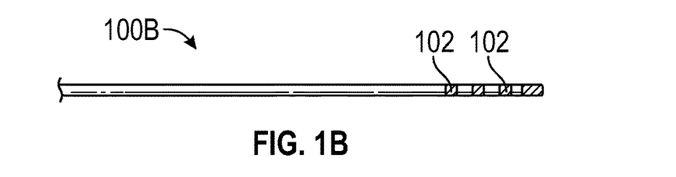
Figure 1C:
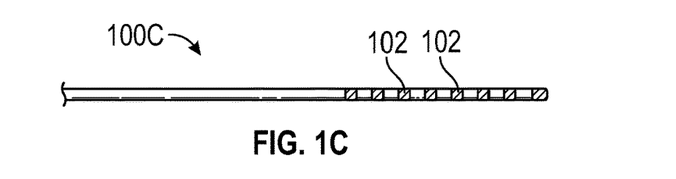
Figure 1D:
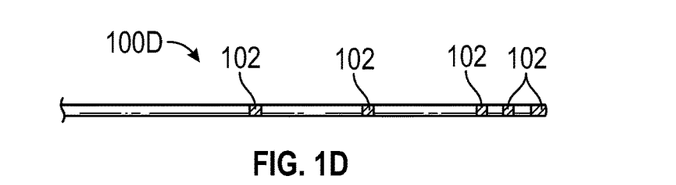
Figure 1E:
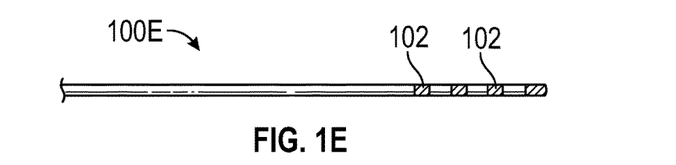
Figure 1F:
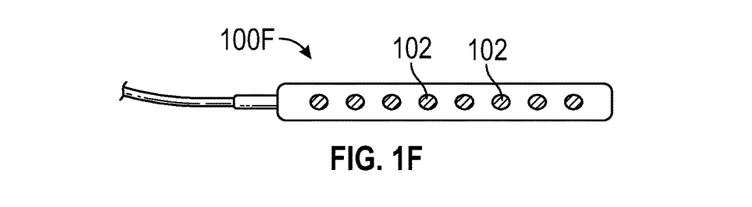
Figure 1G:
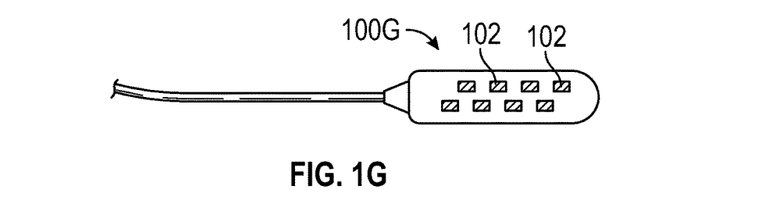
Figure 1H:
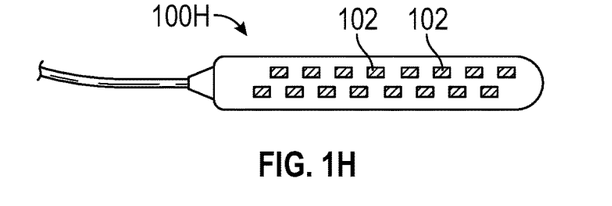
Figure 1I:
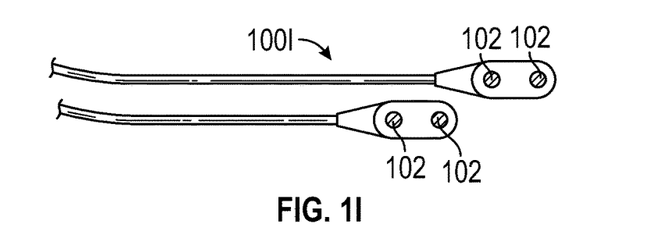
Figure 1J:
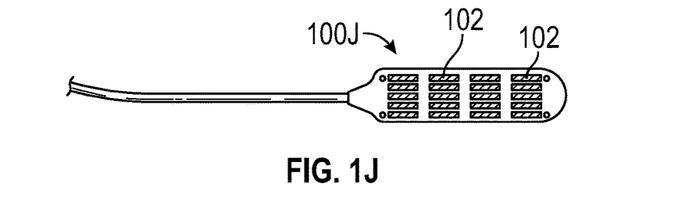
Figure 2:
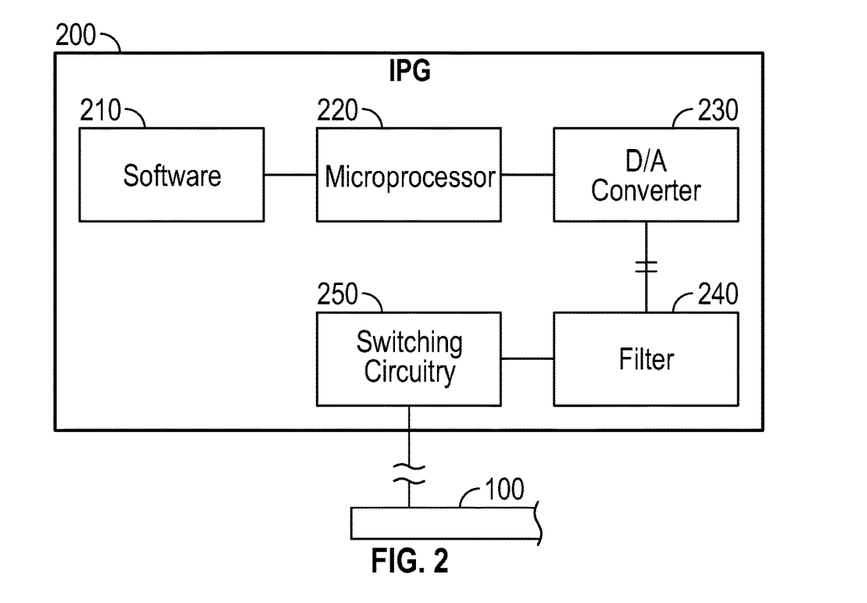
FIG. 2 depicts an implantable pulse generator that may be programmed to generate stimulation according to one representative embodiment.
Figure 3B:
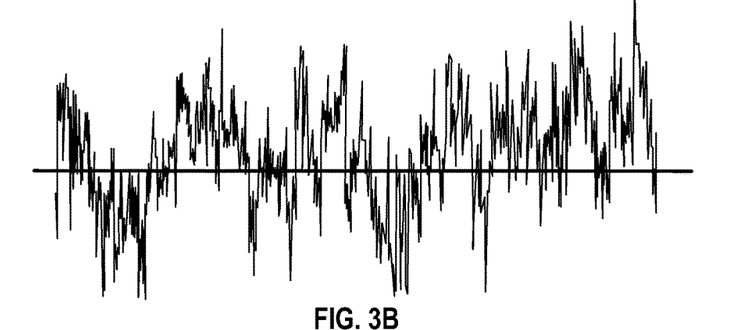
FIG. 3B shows an exemplary pink noise spectrum generated by a power source, for example an external or implantable generator
Figure 4B:
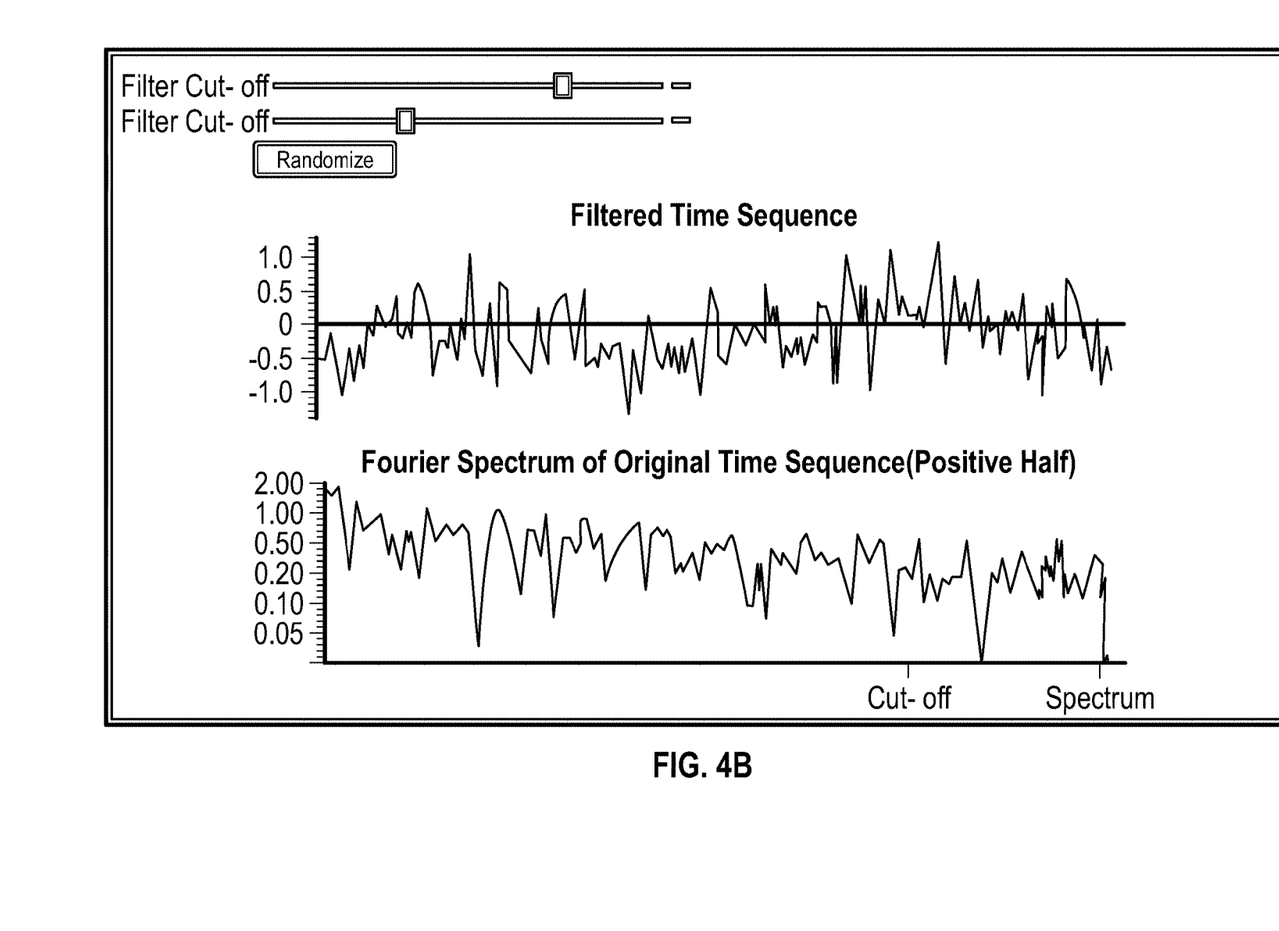
FIG. 4B shows an exemplary spectrum generated by a power source, for example an external or implantable generator.

FIG. 2 depicts an exemplary neuromodulation device that can be used to provide the desired stimulation. Signal parameters are inputted, such as $1/f^\beta$ noise spectrum, for example FIG. 3A or FIG. 4A, into the software or memory 210 and the desired wave pattern or signals are generated using microprocessor 220. A standard digital-to-analog converter 230 receives the calculated digital signals and generates analog output pulses corresponding to the values of the digital signals. The generated output pulses may be outputted from the neuromodulation device through an output capacitor. Optionally, any suitable filter 240 can be used to smooth or shape the signals; however, unsmoothed or unfiltered signals can be transmitted to the switching circuitry 250 which provides the signals to the electrodes 100 thereby stimulating the neuronal tissue using the desired $1/f^\beta$ noise stimulation pattern. As an example, the stimulator design disclosed in U.S. Pat. No. 7,715,912 may be employed to generate stimulation pulses according to the desired stimulation pattern. FIGS. 3B and 4B illustrate exemplary waveforms generated by external generators and provided to the electrodes to stimulate neuronal tissue with the $1/f^\beta$ noise stimulation pattern.

In addition to providing a stimulation waveform similar to that of $1/f^\beta$ noise spectrum; it may be desirable to modify the $1/f^\beta$ noise waveform stimulation pattern. Such modifications can utilize the addition of peak frequencies, such as the addition of an alpha, beta, theta, and/or delta peaks to the $1/f^\beta$ noise spectrum waveform, see for example, FIGS. 5A and 5B. Such frequency peaks can be obtained by using standard peaks or individualizing the frequency peaks. Such information can be communicated to the microprocessor 220 via the software component 210. Thus, the data communicated can comprise standard frequency peaks or comprise individualized frequency peaks or patient specific. The patient specific frequency peaks can be obtained off-line or in real time or on-line, for example prior to implantation or at any time point after implantation, for example, during the initial programming of the IPG. Any suitable signal processing technique may be employed to add the appropriate spectral peaks. For example, a suitable filter may be applied to the noise signal. Alternatively, a separate signal may be generated with a spectral peak about the desired frequency and the separate signal may be added to or superimposed on the noise signal.

Figure 6:
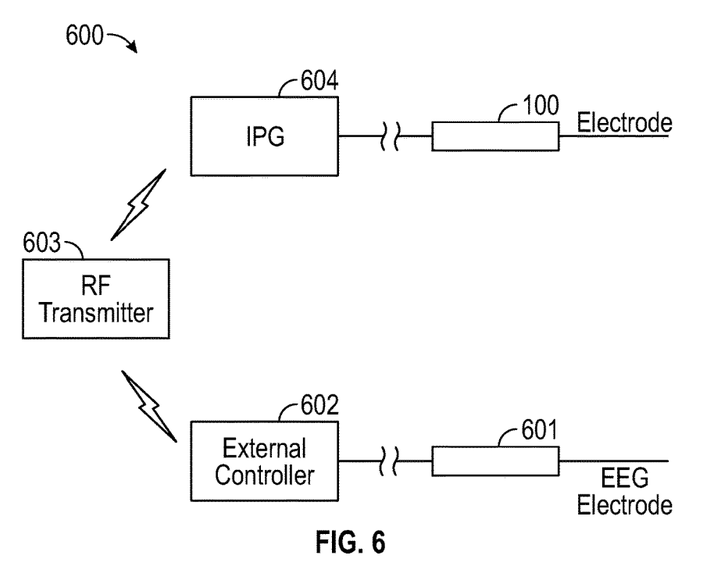
FIG. 6 depicts a stimulation system that can measure or detect given neuronal signals that can be used to modulate the $1/f^\beta$ noise stimulation according to one representative embodiment.

With reference to FIG. 6, with electrodes disposed near, adjacent to, directly next to or within the target neuronal tissue, for example, brain tissue, some representative embodiments utilize the detection and analysis of neuronal activity, such as EEG measurements. Specifically, terminals of the lead such as an EEG lead, may be coupled using respective conductors 601 to external controller that contains suitable circuitry to analyze neuronal activity, for example, an EEG analyzer can be included in the external controller in which the analyzer functions are adapted to receive EEG signals from the electrodes and process the EEG signals to identify frequency peaks, such as LORETA software can be used. Further signal processing may occur on a suitable computer platform within the external controller using available signal processing. The computer platform may include suitable signal processing algorithms (e.g., time domain segmentation, FFT processing, windowing, logarithmic transforms, etc.). Further platforms or algorithms to modify the signals are included in the modification algorithms (e.g., envelope modification, etc). User interface software may be used to present the processed neuronal activity (i.e., specific peak frequency) and combine a specific peak frequency with the $1/f^\beta$ noise stimulation waveform patterns to the transmitter 603 which then transmit, for example, via radio frequency to the IPG 604 which is adapted to provide the $1/f^\beta$ noise stimulation waveform patterns with the peak frequency to achieve stimulation of the target neuronal tissue via electrode 100. This procedure can be performed on-line or off-line. Additionally, IPG 604 preferably comprises circuitry such as an analog-to-digital (AD) converter, switching circuitry, amplification circuitry, transmitters, and/or filtering circuitry.

Still further, it may be desirable to utilize another implantable device that is capable of performing the functions of the external controller. Thus, those of skill in the art can modify an implantable device such that it is capable of detecting/sampling and processing of the signals representative of the neuronal activity/EEG activity. Such a device may include a microprocessor that is capable of performing these activities as well as a transmitter such that the signals can be transmitted via radiofrequency to another implantable device, such as described above in FIG. 6 that is capable of generating the desired signal to the target tissue. Thus, an EEG lead is placed or positioned near the target brain tissue via methods known to those of skill in the art. The EEG lead detects neuronal activity which is relayed to the processor that possesses sufficient computational capacity to collect the information obtained from the EEG electrode, process it to obtain the respective frequency peak desired and/or modulate the frequency peaks and transmit the frequency to an RF transmitter that transmits the respective information to microprocessor located in the stimulation IPG.

Another means to modify the $1/f^\beta$ waveform stimulation pattern is to combine it with tonic stimulation or burst stimulation as described in U.S. Pat. No. 7,734,340, issued Jun. 8, 2010 and U.S. patent application Ser. No. 12/109,098, filed Apr. 24, 2008, both of which are incorporated by reference in their entirety. Thus, a neuromodulation device can be implemented to apply either burst or tonic stimulation using a digital signal processor and one or several digital-to-analog converters. The burst stimulus and/or tonic stimulus waveform could be defined in memory and applied to the digital-to-analog converter(s) for application through electrodes of the medical lead. The digital signal processor could scale the various portions of the waveform in amplitude and within the time domain (e.g., for the various intervals) according to the various burst and/or tonic parameters. A doctor, the patient, or another user of stimulation source may directly or indirectly input stimulation parameters to specify or modify the nature of the stimulation provided.

Thus, a microprocessor and suitable software instructions to implement the appropriate system control can be used to control the burst and/or tonic stimulation in combination with the $1/f^\beta$ stimulation. The processor can be programmed to use "multi-stim set programs" which are known in the art. A "stim set" refers to a set of parameters which define a pulse to be generated. For example, a stim set defines pulse amplitude, a pulse width, a pulse delay, and an electrode combination. The pulse amplitude refers to the amplitude for a given pulse and the pulse width refers to the duration of the pulse. The pulse delay represents an amount of delay to occur after the generation of the pulse (equivalently, an amount of delay could be defined to occur before the generation of a pulse). The amount of delay represents an amount of time when no pulse generation occurs. The electrode combination defines the polarities for each output which, thereby, controls how a pulse is applied via electrodes of a stimulation lead. Other pulse parameters could be defined for each stim set such as pulse type, repetition parameters, etc. Still further, the $1/f^\beta$ waveform stimulation pattern alone or in combination with either burst and/or tonic may be implemented such that the stimulation occurs either sequentially, randomly or pseudo-sequentially over multiple poles or electrodes on the stimulation lead.

In certain embodiments, the stimulation parameters may comprise a burst stimulation having a frequency in the range of about 1 Hz to about 300 Hz in combination with a tonic stimulation having a frequency in the range of about 1 Hz to about 300 Hz. Those of skill in the art realize that the frequencies can be altered depending upon the capabilities of the IPGs that are utilized. More particularly, the burst stimulation may be at about 6, 18, 40, 60, 80, 100, 150, 200, 250 or 300 Hz consisting of 5 spikes with 1 ms pulse width, 1 ms interspike interval in combination with $1/f^\beta$ signals interspersed between or around the burst or prior to or after the burst or in any variation thereof depending upon the efficacy of treatment. Still further, $1/f^\beta$ signals or stimulation paradigm as described herein may be used in combination with about 6, 18, 40, 60, 80, 100, 150, 200, 250, 300 Hz tonic stimulation interspersed between or around the $1/f^\beta$ signals or stimulation paradigm, or any variation thereof depending upon the efficacy of treatment and the capabilities of the IPG.

Still further, those of skill in the art recognize that burst firing refers to an action potential that is a burst of high frequency spikes (300-1000 Hz) (Beurrier et al., 1999). Burst firing acts in a non-linear fashion with a summation effect of each spike and tonic firing refers to an action potential that occurs in a linear fashion.

Yet further, burst can refer to a period in a spike train that has a much higher discharge rate than surrounding periods in the spike train (N. Urbain et al, 2002). Thus, burst can refer to a plurality of groups of spike pulses. A burst is a train of action potentials that, possibly, occurs during a 'plateau' or 'active phase', followed by a period of relative quiescence called the 'silent phase' (Nunemaker, Cellscience Reviews Vol 2 No. 1, 2005.) Thus, a burst comprises spikes having an inter-spike interval in which the spikes are separated by 0.5 milliseconds to about 100 milliseconds. Those of skill in the art realize that the inter-spike interval can be longer or shorter. Yet further, those of skill in the art also realize that the spike rate within the burst does not necessarily occur at a fixed rate; this rate can be variable. A spike refers to an action potential. Yet further, a "burst spike" refers to a spike that is preceded or followed by another spike within a short time interval (Matveev, 2000), in other words, there is an inter-spike interval, in which this interval is generally about 100 ms but can be shorter or longer, for example 0.5 milliseconds.

Figure 7:
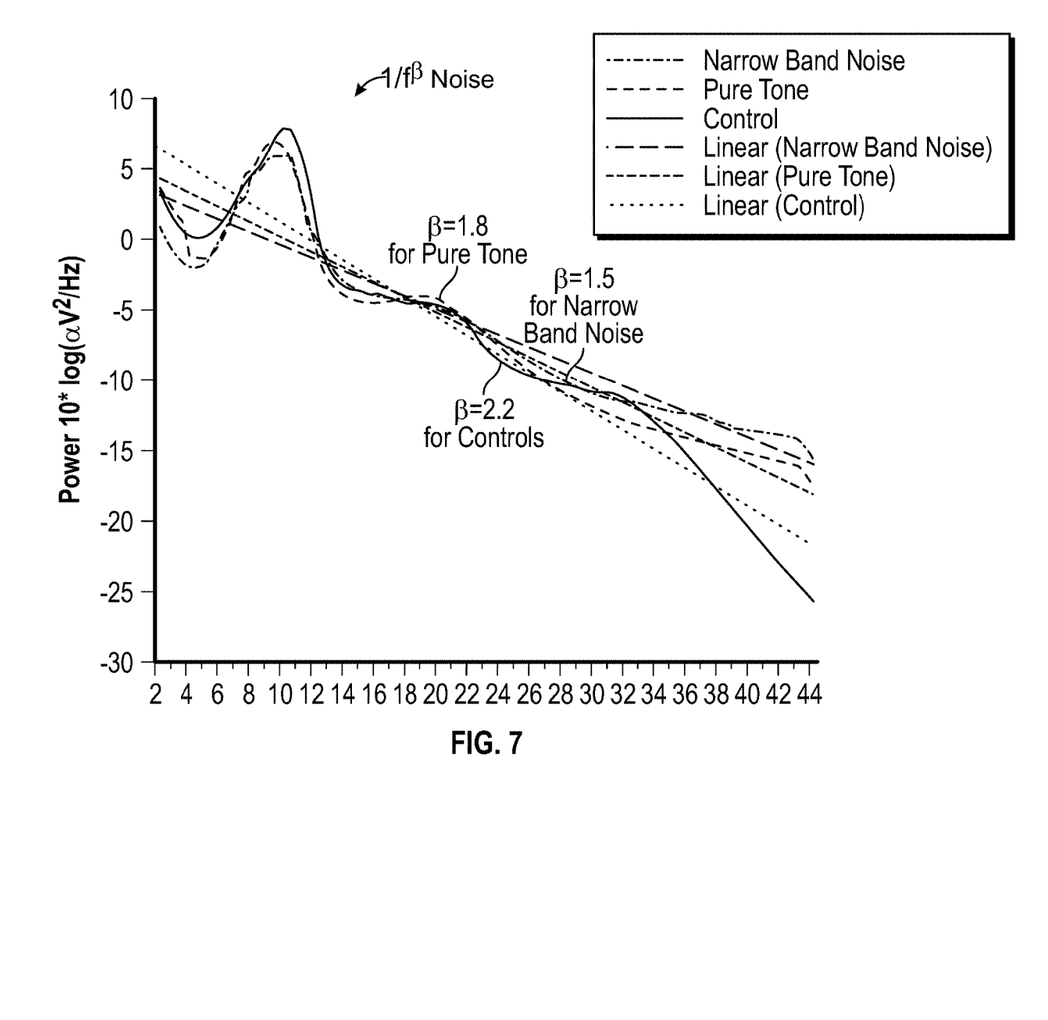
FIG. 7 illustrates a $1/f^\beta$ spectrum at rest for normal and tinnitus patients. $\beta$ is 2.2 for healthy controls, 1.5 for noise-like tinnitus and 1.8 for pure tone tinnitus.

Still further, it may be of interest to use a system that includes a processor that determines whether the patient is in a sleep state, and controls therapy based upon the sleep state. The sleep state may be relevant for $1/f^\beta$ noise stimulation therapy if during a given sleep stage the patient's frequency spectrum changes, for example, the high frequency is adjusted such that the spectrum moves from pink or brown noise to black noise. For example, FIG. 7 shows $1/f^2$ (brown noise) activity at rest in a human tinnitus patient and in normal patients. At rest, the brain has an activity at $1/f^2$ (brown noise) for the normal patients and the tinnitus patients tend to have an activity at $1/f^{1-2}$ (between pink and brown noise)

As referred to herein, the sleep state may refer to a state in which patient is intending on sleeping (e.g., initiating thoughts of sleep), is at rest, is attempting to sleep or has initiated sleep and is currently sleeping. In addition, the processor may determine a sleep stage of the sleep state based on a biosignal detected within brain the patient and control therapy delivery to patient based on a determined sleep stage. Examples of biosignals include, but are not limited to, electrical signals generated from local field potentials within one or more regions of brain, such as, but not limited to, an electroencephalogram (EEG) signal or an electrocorticogram (ECOG) signal. The biosignals that are detected may be detected within the same tissue site of brain as the target tissue site for delivery of electrical stimulation. In other examples, the biosignals may be detected within another tissue site.

Within a sleep state, the patient may be within one of a plurality of sleep stages. Example sleep stages include, for example, Stage 1 (also referred to as Stage N1 or S1), Stage 2 (also referred to as Stage N2 or S2), Deep Sleep (also referred to as slow wave sleep), and rapid eye movement (REM). The Deep Sleep stage may include multiple sleep stages, such as Stage N3 (also referred to as Stage S3) and Stage N4 (also referred to as Stage S4). In some cases, the patient may cycle through the Stage 1, Stage 2, Deep Sleep, REM sleep stages more than once during a sleep state. The Stage 1, Stage 2, and Deep Sleep stages may be considered non-REM (NREM) sleep stages.

Figure 8:
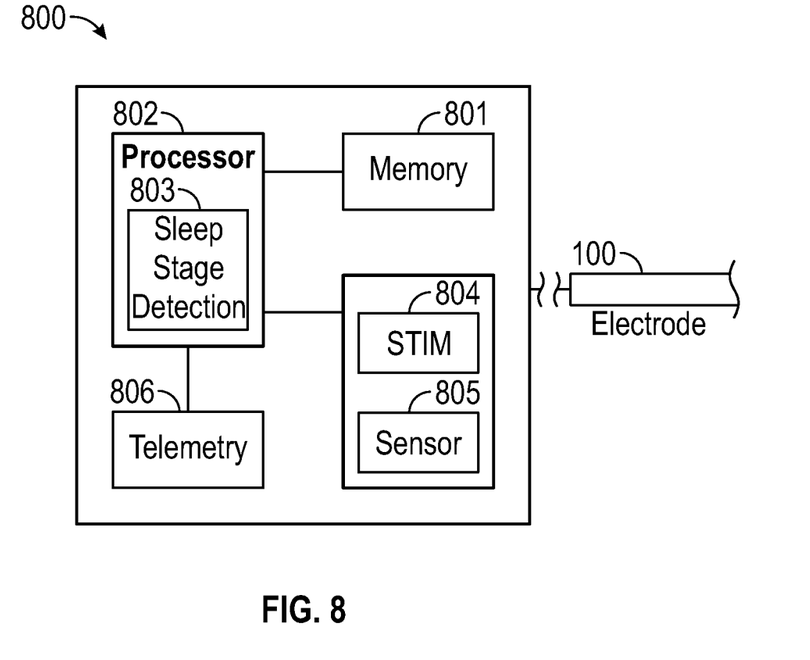
FIG. 8 depicts a stimulation system that can sense and/or monitor sleep stage that can be used to after therapy.

FIG. 8 shows an exemplary implantable neuromodulation device 800 that can be used to determine a stage of sleep and adjust therapy. For example, the device may include, processor 802, memory 801, stimulation generator 804, sensing module 805, telemetry module 806, and sleep stage detection module 803. Although sleep stage detection module 803 is shown to be a part of processor 802 in FIG. 7, in other examples, sleep stage detection module 803 and processor 802 may be separate components and may be electrically coupled, e.g., via a wired or wireless connection.

Figure 9:
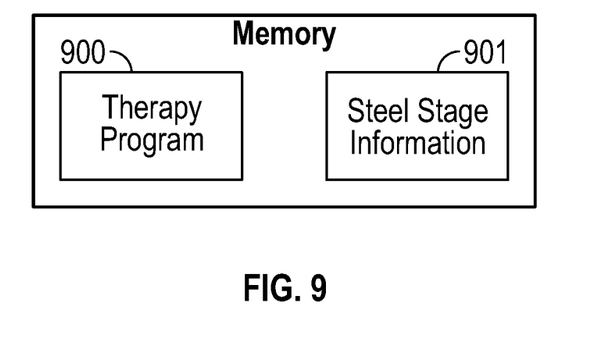
FIG. 9 shows modules within the memory of FIG. 8.

Memory 801, as shown in FIG. 9, may include any volatile or non-volatile media, such as a random access memory (RAM), read only memory (ROM), non-volatile RAM (NVRAM), electrically erasable programmable ROM (EEPROM), flash memory, and the like. Memory 801 may store instructions for execution by processor 802 and information defining therapy delivery for the patient, such as, but not limited to, therapy programs or therapy program groups, information associating therapy programs with one or more sleep stages, thresholds or other information used to detect sleep stages based on biosignals, and any other information regarding therapy of the patient. Therapy information may be recorded in memory 801 for long-term storage and retrieval by a user. As described in further detail with reference to FIG. 9, memory 801 may include separate memories for storing information, such as separate memories for therapy programs 900, and sleep stage information 901. Yet further, other memories that may be stored may include patient information, such as information relating to specific peak frequencies, or information relating to $1/f^\beta$ stimulation.

It is also envisaged that the recording electrode can be used to record or detect sleep stage or when a subject is not in a sleep stage, the recording electrode can be used to detect a change in the normal spectral composition of the noise and adjust the parameters of the stimulation therapy, for example, adjust the stimulation factors such as drowsiness, stress, depression, excitement, arousal, alcohol or other drug intake etc.

V. Treating Neurological Conditions

The present stimulation method acts to stimulate neuronal tissue which in turn stimulate the neuronal tissue to cause/ allow the tissue to act in the best interest of the host through use of the its natural mechanisms.

Accordingly, the present methods and/or devices relate to modulation of neuronal activity to affect neurological, neuropsychological or neuropsychiatric activity. The present method finds particular application in the modulation of neuronal function or processing to affect a functional outcome. The modulation of neuronal function is particularly useful with regard to the prevention, treatment, or amelioration of neurological, psychiatric, psychological, conscious state, behavioral, mood, and thought activity (unless otherwise indicated these will be collectively referred to herein as "neurological activity" which includes "psychological activity" or "psychiatric activity"). When referring to a pathological or undesirable condition associated with the activity, reference may be made to a neurological disorder which includes "psychiatric disorder" or "psychological disorder" instead of neurological activity or psychiatric or psychological activity. Although the activity to be modulated usually manifests itself in the form of a disorder such as a attention or cognitive disorders (e.g., Autistic Spectrum Disorders); mood disorder (e.g., major depressive disorder, bipolar disorder, and dysthymic disorder) or an anxiety disorder (e.g., panic disorder, posttraumatic stress disorder, obsessive-compulsive disorder and phobic disorder); neurodegenerative diseases (e.g., multiple sclerosis, Alzheimer's disease, amyotrophic lateral sclerosis (ALS), Parkinson's disease, Huntington's Disease, Guillain-Barre syndrome, myasthenia gravis, and chronic idiopathic demyelinating disease (CID)), movement disorders (e.g., dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism), epilepsy, tinnitus, pain, phantom pain, diabetes neuropathy, one skilled in the art appreciates that the invention may also find application in conjunction with enhancing or diminishing any neurological or psychiatric function, not just an abnormality or disorder. Neurological activity that may be modulated can include, but not be limited to, normal functions such as alertness, conscious state, drive, fear, anger, anxiety, repetitive behavior, impulses, urges, obsessions, euphoria, sadness, and the fight or flight response, as well as instability, vertigo, dizziness, fatigue, photophobia, concentration dysfunction, memory disorders, headache, dizziness, irritability, fatigue, visual disturbances, sensitivity to noise (misophonia, hyperacusis, photophobia), judgment problems depression, symptoms of traumatic brain injury (whether physical, emotional, social or chemical), autonomic functions, which includes sympathetic and/or parasympathetic functions (e.g., control of heart rate), somatic functions, and/or enteric functions. Thus, the present methods and/or devices encompass modulation of central and/or peripheral nervous systems.

Other neurological disorders can include, but are not limited to headaches, for example, migraine, trigeminal autonomic cephalgia (cluster headache (episodic and chronic)), paroxysmal hemicrania (episodic and chronic) hemicrania continua, SUNCT (shortlasting unilateral neuralgiform headache with conjunctival injection and tearing) cluster tic syndrome, trigeminal neuralgia, tension type headache, idiopathic stabbing headache, etc. The neurostimulation device can be implanted intracranially or peripherally, for example, but not limited to implanting a neurostimulation device occipitally for the treatment of headaches.

Autonomic and/or enteric nervous system disorders that can be treated using the stimulation system and/or method of the present invention include, but are not limited to hypertension, neurosis cordis or heart rhythm disorders, obesity, gastrointestinal motion disorders, respiratory disorders, diabetes, sleep disorders, snoring, incontinence both urologic and gastrointestinal, sexual dysfunction, chronic fatigue syndrome, fibromyalgia, whiplash associated symptoms, post-concussion syndrome, posttraumatic stress disorder etc.

Yet further it disorders may also be treated using the stimulation system and/or method of the present invention. This is based on the fact that the immune system senses antigens coordinates' metabolic, endocrine and behavioral changes that support the immune system and modulates the immune system via neuroendocrine regulation and direct immune cell regulation. Such immunological disorders include, such as allergy, rhinitis, asthma, rheumatoid arthritis psoriasis arthritis, lupus erythematosus disseminatus, multiple sclerosis and other demyelinating disorders, autoimmune thyroiditis Crohn's disease, diabetes mellitus etc.

Still further tumoral disorders, both malignant and benign may also be treated using the stimulation system and/or method of the present invention. This is based on the fact that tumoral behavior is linked to immunological function. This is seen in immunodeficiency syndromes such as AIDS and hematological disorders, where multiple and different tumors develop. In this setting neuromodulation could indirectly influence tumoral behavior.

Yet further neuroendocrine disorders may also be treated using the stimulation system and/or method of the present invention. Such disorders are stress reactions, hypothalamic-pituitary axis dysfunction, etc.

Yet further functional disorders may also be treated using the stimulation system and/or method of the present invention. Such disorders can be anorexia bulimia, phobias, addictions, paraphilia psychosis, depression, bipolar disorder, kleptomania aggression, or antisocial sexual behavior. One skilled in the art appreciates that the invention may also find application in conjunction with enhancing or diminishing any neurological or psychiatric function, not just an abnormality or disorder.

Using the above described stimulation system, the predetermined site or target area is stimulated in an effective amount or effective treatment regimen to decrease, reduce, modulate or abrogate the neurological disorder or condition. Thus, a subject or patient is administered a therapeutically effective stimulation so that the subject has an improvement in the parameters relating to the neurological disorder or condition including subjective measures such as, for example, neurological examinations and neuropsychological tests (e.g., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS, CGI, N-BAC, or Yale-Brown Obsessive Compulsive score (Y-BOCS)), motor examination, visual analog scale (VAS) and cranial nerve examination, and objective measures including use of additional psychiatric medications, such as anti-depressants, or other alterations in cerebral blood flow or metabolism and/or neurochemistry.

Patient outcomes may also be tested by health-related quality of life (HRQL) measures: Patient outcome measures that extend beyond traditional measures of mortality and morbidity, to include such dimensions as physiology, function, social activity, cognition, emotion, sleep and rest, energy and vitality, health perception, normal eating habits or behaviors (i.e., regained appetite or reduced appetite) and general life satisfaction. (Some of these are also known as health status, functional status, or quality of life measures.)

Treatment regimens may vary as well, and often depend on the health and age of the patient. Obviously, certain types of disease will require more aggressive treatment, while at the same time; certain patients cannot tolerate more taxing regimens. The clinician will be best suited to make such decisions based on the known subject's history.

For purposes of this invention, beneficial or desired clinical results include, but are not limited to, alleviation of symptoms, improvement of symptoms, diminishment of extent of disease, stabilized (i.e., not worsening) state of disease, delay or slowing of disease progression, amelioration or palliation of the disease state, and remission (whether partial or total), whether objective or subjective. The improvement is any observable or measurable improvement. Thus, one of skill in the art realizes that a treatment may improve the patient condition, but may not be a complete cure of the disease.

In certain embodiments, in connection with improvement in one or more of the above or other neurological disorders, the electrical stimulation may have a "brightening" effect on the person such that the person looks better, feels better, moves better, thinks better, and otherwise experiences an overall improvement in quality of life, (e.g., self confidence, alleviating shyness, distrust etc).

In certain embodiments, the neuromodulation method described herein is utilized to treat a subject suffering from or suspected of suffering from tinnitus. Thus, a subject is administered a therapeutically effective stimulation so that the subject has an improvement in the parameters relating to tinnitus including informal questioning of the subject, formal subjective testing and analysis according to one or more audiology test, for example the Goebel tinnitus questionnaire or other validated tinnitus questionnaires, audiometry, tinnitus matching, impedance, BAEP, and OAE. The improvement is any observable or measurable improvement. Thus, one of skill in the art realizes that a treatment may improve the patient condition, but may not be a complete cure of the disease.

In other embodiments, the neuromodulation method described herein is utilized to treat a subject suffering from or suspected of suffering from pain. One example of a method for pain measurement is the use of the Visual Analog Scale (VAS). In the VAS patients are asked to rank their pain by making a mark on a bar that is labeled "no pain" on one end, and "pain as bad as possible" on the other end. Patients may mark the bar anywhere between the two opposite poles of perceived pain sensation. This mark can then be given any quantitative value such as fractional, decimal or integer values by the clinician and used as a semi-quantitative pain measurement. In various tests for pain severity, patients may rank their pain on a scale between zero and ten, by a scale of faces depicting various emotions from happy to very sad and upset, and by answering a variety of questions describing the pain. In preferred embodiments, the patient's pain is assessed prior to and during a trial implantation procedure. In other embodiments, informal subjective questioning of the person, and/or formal subjective testing and analysis may be performed to determine whether the subject's pain has sufficiently improved throughout trial stimulation.

In addition to utilizing pain scores and grading and objective measures including use of additional pain medications (e.g., reduction in the amount of medication consume or elimination of the consumption of pain medications), other methods to determine improvement of a patient's pain may comprise administering various standardized questionnaires or tests to determine the patient's neuropsychological state as described above.

If the subject's neurological disorder/disease has not sufficiently improved, or if the reduction of the neurological disorder/disease is determined to be incomplete or inadequate during an intra-implantation trial stimulation procedure, stimulation lead may be moved incrementally or even re-implanted, one or more stimulation parameters may be adjusted, or both of these modifications may be made and repeated until at least one symptom associated with the neurological disorder/disease has improved.

Where appropriate, post-implantation trial stimulation may be conducted to determine the efficacy of various types of burst and tonic stimulation. Examples of efficacy metrics may include the minimum required voltage for a given protocol to achieve maximum and/or therapeutic benefits to the neurological disease and/or disorder. Efficacy metrics may also include a measurement of the presence and/or degree of habituation to a given protocol over one or more weeks or months, and any necessary modifications made accordingly. Such assessments can be conducted by suitable programming, such as that described in U.S. Pat. No. 5,938,690, which is incorporated by reference here in full. Utilizing such a program allows an optimal stimulation therapy to be obtained at minimal power. This ensures a longer battery life for the implanted systems.

In certain embodiments, it may be desirable for the patient to control the therapy to optimize the operating parameters to achieve increased or optimized the treatment. For example, the patient can alter the pulse frequency, pulse amplitude and pulse width using a hand held radio frequency device that communicates with the IPG. Once the operating parameters have been altered by the patient, the parameters can be stored in a memory device to be retrieved by either the patient or the clinician. Yet further, particular parameter settings and changes therein may be correlated with particular times and days to form a patient therapy profile that can be stored in a memory device.

VI. Example

The following are examples provided herein. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In the clinical setting patients were implanted to treat pain or tinnitus.

Materials and Methods

Patients having spasticity, phantom pain, facial pain or tinnitus were implanted with electrodes for stimulation therapy using $1/f^\beta$ noise stimulation patterns. The patients were implanted with the electrodes (Lamitrode 44 stimulation lead available from ANS Medical, Plano, Tex., USA). In most patients, the electrodes (Lamitrode 44 stimulation lead available from ANS Medical Plano, Tex., USA) were implanted in the auditory cortex, and one patient was implanted with a cervical dorsal column stimulation electrode (Lamitrode 44 stimulation lead). Prior to the use of $1/f^\beta$ noise stimulation patterns, all patients underwent burst stimulation at 6, 18, or 40 Hz consisting of 5 spikes with 1 ms pulse width, 1 ms interspike interval in a charged balanced manner and 6, 18, or 40 Hz tonic mode interspersed between or around the bursts. The stimuli were delivered by an 8 channel digital neurostimulator (DS8000, World Precision Instruments, Hertfordshire, England/Sarasota Fla., USA), capable of delivering tonic and burst mode stimulation. Next, $1/f^\beta$ noise stimulation patterns was used to determine if $1/f^\beta$ noise stimulation patterns resulted in more improvement of the symptoms or reduces the risk of epileptic events. Three patients received constant $1/f^\beta$ noise stimulation for >1.5 hrs without an epileptic event. The stimuli were delivered by an 8 channel digital neurostimulator (DS8000, World Precision Instruments, Hertfordshire, England/Sarasota, Fla., USA), capable of delivering $1/f^\beta$ noise stimulation, see for example FIGS. 3A and 3B.

Figure 5A:
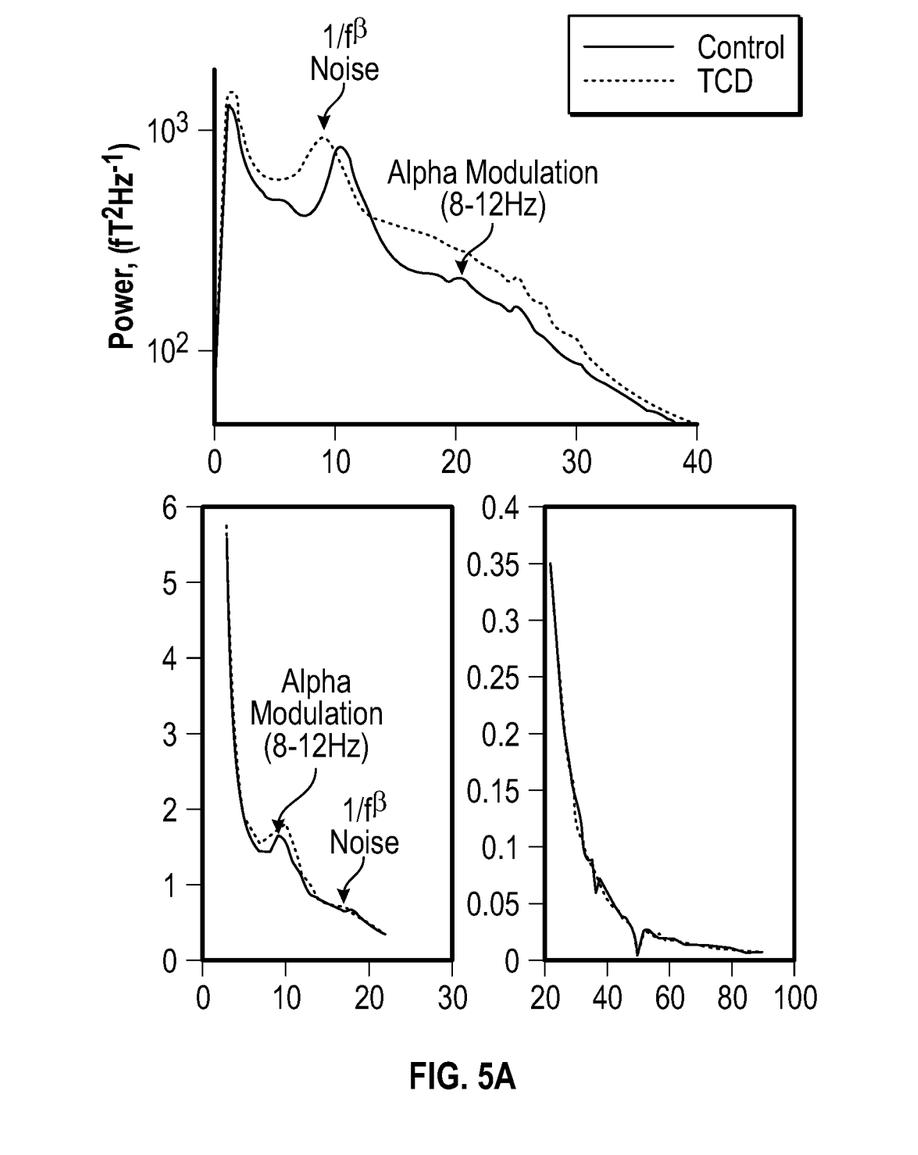
FIG. 5A shows $1/f^\beta$ noise modulated at alpha frequencies and FIG. 5B at $1/f^\beta$ noise modulated at beta frequencies.
Figure 5B:
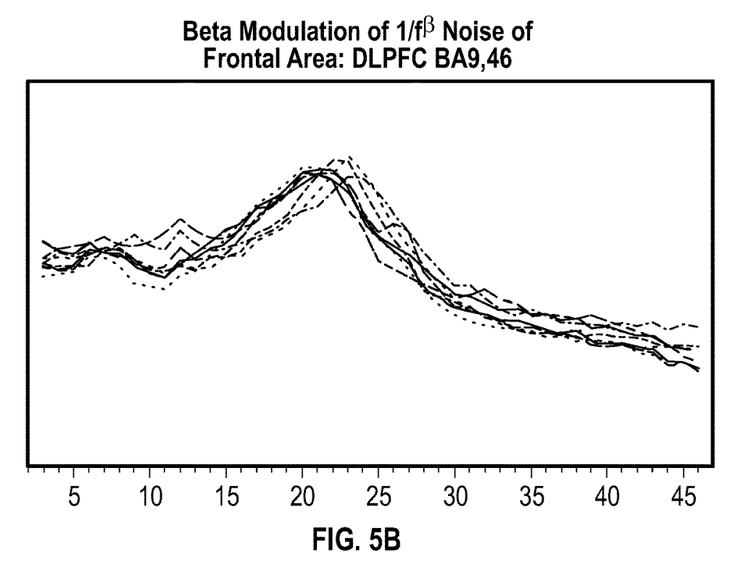

In another patient, the stimulation was altered by adding a beta peak frequency; see for example, FIGS. 5A and 5B.

Results

The below Table 1 shows VAS scores for patients that had burst, tonic and then had noise stimulation or $1/f^\beta$ stimulation. The table shows that by $1/f^\beta$ stimulation parameters patients suffering tinnitus, spasticity, phantom pain and facial can be treated with improved benefits of no epileptic events measured during constant stimulation for >1.5 hrs. Yet further, the below table also shows that if the patient responds to burst or tonic stimulation, then the patient will respond to $1/f^\beta$ stimulation parameters, and if the patient does not respond to burst or tonic stimulation, then they will probably not respond to $1/f^\beta$ stimulation parameters. This lack of response may be an indication that the stimulation site is not optimal and a different site should be examined or investigated.

Noise Stimulation

| | Pre-operative | prestimulation | Post 1/f$^\beta$ noise pulse alpha peak modulated stimulation |
|---|---|---|---|
| spasticity | 7 | 6 | 4 |
| phantom pain | 9 | 5.5 | 3.5 |
| dorsal column stimulation | 8 | 6 | 4 |
| tinnitus | 8 | 7 | 6.5 |
| tinnitus | 10 | 9.5 | 8 |
| tinnitus | 10 | 7 | 7 |
| Facial pain | 7 | 6.5 | 5.5 |
| tinnitus | 9 | 7 | 6 |
| Tinnitus | 9 | 8 | 7 |
| Tinnitus | 8 | 8 | 8 |
| Tinnitus | 10 | 10 | 10 |
| Tinnitus | 8 | 8 | 8 |
| Facial pain | 8 | 8 | 8 |

*= after tonic or burst stimulation

CONCLUSIONS

At least three patients were stimulated constantly for more than one hour without inducing an epileptic event Thus, this type of stimulation paradigm is anti-epileptic and will prevent habituation because it mimics natural oscillations and has a longer lasting residual inhibition which will limit battery utilization and limit the amount of current that is used to stimulate the brain.

As will be recognized by those skilled in the art, the innovative concepts described in the present application can be modified and varied over a wide range of applications. Accordingly, the scope of patented subject matter should not be limited to any of the specific exemplary teachings discussed above, but is instead defined by the following claims.

What is claimed:

1. A method of stimulating nerve tissue of a patient using a pulse generator to treat chronic pain of the patient, the method comprising:
   generating, by a pulse generator, a set of electrical pulses that exhibit a power spectral density over a first frequency range, wherein (A) the power spectral density of the stimulation therapy generally follows a function of 1/f$^\beta$, except for power amplitude modulation within a second frequency range more narrow than the first frequency range, (B) β is greater than one (1) and f is a variable representing frequency, (C) the power spectral density is increased by the power amplitude modulation within the second frequency range, (D) the second frequency range includes a peak frequency with a greatest increased power amplitude modulation from power defined by the function of 1/f$^\beta$, and (E) the peak frequency is within an alpha frequency range of eight (8) to twelve (12) Hertz;
   providing the set of electrical pulses from the pulse generator to at least one stimulation lead; and
   applying the set of electrical pulses to nerve tissue of the patient via one or several electrodes of the at least one stimulation lead to treat chronic pain of the patient.

2. The method of claim wherein 1 wherein β is selected from values greater than two (2).

3. The method of claim 1 wherein the generating comprises (1) generating a first digital signal, (2) filtering the first digital signal to generate a second digital signal generally following a function of 1/f$^\beta$, except for increased power amplitude within the second frequency range including the peak frequency, and (3) using the second digital signal to generate the set of electrical pulses.

4. The method of claim 1 further comprising:
   automatically detecting a sleep state by the implantable pulse generator; and
   automatically modifying a value of β for use by the generating during the sleep state.

5. The method of claim 1 wherein the set of electrical pulses are applied to a spinal cord of the patient.

6. The method of claim 1 wherein the set of electrical pulses are applied to a nerve root ganglion of the patient.

7. The method of claim 1 wherein the set of electrical pulses are applied to a peripheral nerve.

8. The method of claim 1 wherein the applying comprises applying respective pulses of the set of electrical pulses using different electrodes of at least one stimulation lead.

9. The method of claim 8 wherein the different electrodes are selected sequentially.

10. The method of claim 8 wherein the different electrodes are randomly selected.

11. The method of claim 1 further comprising defining an upper frequency bound for the first frequency range.

12. The method of claim 1 further comprising defining a low frequency bound for the first frequency range.

* * * * *